United States Patent
Dang et al.

(10) Patent No.: US 11,857,931 B2
(45) Date of Patent: Jan. 2, 2024

(54) PROCESS FOR PRODUCTION OF NANO-MICROEMULSION SYSTEM OF PLANT OIL TRIGLYCERIDES

(71) Applicant: WAKAMONO joint stock company, Ho Chi Minh (VN)

(72) Inventors: Hong Ngoc Thi Dang, Ho Chi Minh (VN); Nam Hai Lai, Ho Chi Minh (VN)

(73) Assignee: Wakamono Joint Stock Company, Ho Chi Minh (VN)

( * ) Notice: Subject to any disclaimer, the term of this patent is extended or adjusted under 35 U.S.C. 154(b) by 839 days.

(21) Appl. No.: 16/931,191

(22) Filed: Jul. 16, 2020

(65) Prior Publication Data
US 2020/0346174 A1    Nov. 5, 2020

(51) Int. Cl.
*B32B 9/00* (2006.01)
*B01F 23/411* (2022.01)
*B01F 23/80* (2022.01)
B82Y 30/00 (2011.01)
B01F 23/41 (2022.01)
B01F 101/40 (2022.01)

(52) U.S. Cl.
CPC ........ *B01F 23/4111* (2022.01); *B01F 23/802* (2022.01); *B01F 23/4143* (2022.01); *B01F 23/4145* (2022.01); *B01F 2101/40* (2022.01); *B82Y 30/00* (2013.01)

(58) Field of Classification Search
CPC ............................. B01F 23/4111; B82Y 30/00
USPC .......................................... 428/408; 423/448
See application file for complete search history.

(56) References Cited

FOREIGN PATENT DOCUMENTS

WO    WO2018/170235    *   9/2018   ............... A61K 9/14

* cited by examiner

*Primary Examiner* — Daniel H Miller
(74) *Attorney, Agent, or Firm* — Fulwider Patton LLP

(57) ABSTRACT

The application refers to process for production of a nano-microemulsion system of plant oil triglycerides, including: (i) preparing a dispersed phase plant oil triglyceride; (ii) preparing a carrier made from a mixture of propylene glycol monocaprylate and lecithin by a weight ratio of 5-6:1-1.5; (iii) adding the carrier to the dispersed phase by a weight ratio of 3-4:1-1.5, wherein the dispersed phase temperature is maintained between 60-100° C. while stirring under vacuum, followed by introduction of the whole mixture through the high-pressure microjet homogenizer; (iv) adding Tween 80 and Tween 60 to the solution mixture obtained in step (iii) by a weight ratio of 3-4:1-1.5:1-1.5, wherein the temperature of the dispersed phase is continuously maintained between 60-100° C. while stirring under vacuum; and (v) forming a nano-microemulsion system of plant oil triglycerides by cooling the mixture, followed by homogenization of the mixture by ultrasonication to achieve a droplet size of less than 100 nm, quality control of the resultant product by dissolution thereof in water and measurement of the transparency, in which if the required transparency is not met, continue to heat and measure the transparency until the required transparency is met, then stop the reaction, and emulsification of the mixture to obtain a nano-microemulsion system of plant oil triglycerides.

4 Claims, 1 Drawing Sheet

PROCESS FOR PRODUCTION OF NANO-MICROEMULSION SYSTEM OF PLANT OIL TRIGLYCERIDES

CROSS-REFERENCES TO RELATED APPLICATIONS

This application claims priority from Vietnam Application No. 1-2020-00125, filed Jan. 7, 2020, incorporated by reference in its entirety.

FIELD OF INVENTION

The application refers to a process for production of nano-microemulsion system of plant oil triglycerides.

BACKGROUND OF THE INVENTION

Triglycerides are the main component of plant oil triglycerides and animal fats. Oils such as coconut oil, avocado oil, jojoba oil, argan oil, olive oil, almond oil, etc., are composed of fatty acids, and triglycerides. The oils contain components such as vitamins, minerals, antioxidants, and a plurality of beneficial nutrients, with a variety of applications in cosmetics, pharmaceuticals, and food. However, they all have disadvantages such as water insolubility, and instability during thermal processing and storage, which has made it difficult to apply these on an industrial scale.

Therefore, it is necessary to improve the stability, reduce the denaturation during production, improve the water dispersibility, and increase the bioavailability of oils. This topic has also attracted great concerns over studies on nanotechnology as a novel technological application to form a delivery system and increase the bioavailability of compounds which are generally attracting research intentions, one of which is to develop a process for production of a nano-microemulsion system of plant oil triglycerides.

In 2017, Carla Arancibia et al studied the topic of "Comparing the effectiveness of natural and synthetic emulsifiers on oxidative and physical stability of avocado oil-based nano-emulsions". Comparative study results between Tween 80 and lecithin show that Tween 80 functioned better. However, this study was conducted only in experimental models, and has not been applied in the industry. Further, the study only stopped at the comparing step to select a more optimal compound.

Chinese Patent Publication No. CN106723052A refers to a method for preparing omega-rich linseed oil nanoemulsions. The method produced large-sized microdroplets of about 500 nm, and a linseed oil content of less than 20% which was water insoluble.

In 2018, Sirikarn Pengona et al, in their research on "The effect of surfactant on the physical properties of coconut oil nanoemulsions", developed a coconut oil that was compatible with water through nanoemulsification. Results show that the coconut oil nano-droplets using polyethylene glycol octyl (PGO) phenyl ether, polyoxyethylene sorbitan monostearate (POS), and polyethylene glycol hydrogenated castor oil (PHC) as surfactants give low creaming indices that indicate excellent stability, while compounds containing sodium lauryl sulfate (SLS) and poloxame 407 (PLX) give higher creaming indices that indicate lower physical stability. The droplet size of nano-droplets decreased from 33 μm to below 200 nm with an increase in PHC from 1% to 10% by weight. However, in this study, the droplets have a size of 200 nm, the droplets are not uniform, and the oil ratio in the emulsion is only 5%, which made it unstable in water.

In 2013, Hiren C. Patel et al, in their research on "Formulation and evaluation of o/w nanoemulsion of ketoconazole", produced nano-droplets of 100-1000 nm, which was the optimized formulation for formation of an oil-in-water microemulsion system for in vivo laboratory studies to make an increase in the bioavailability of the oil. However, this formulation has only been applied on an experimental scale, the droplet size was even larger than 100 nm, and the droplets were not uniform, making it difficult to apply on an industrial scale.

International Publication No. WO 2009/121069 A2 (Compositions and methods for the preparation of nanoemulsions) refers to the production of droplets of 100 nm, 50 nm, 25 nm in the microemulsion system based on the ratio of the surfactants to the oils. In this invention, the inventors investigated different surfactants and ratios to achieve a desired droplet size, and an oil ratio in the system of less than 20%. This was performed on a laboratory scale, and the study stopped at the steps of investigating the ratios, wherein the prolonged performance time, and the samples in trace amounts, and complicated machine uses made it difficult to apply on an industrial scale.

U.S. Pat. No. 7,399,479 B2 (Microemulsions, especially for skin or hair treatment) introduces a microemulsion system applicable to skincare and hair care. This patent compares the effects of between the oil phase and the aqueous phase within an emulsion for production of cosmetic products. Most preferably, clear, transparent, or blurred microemulsion droplets contain 20-60% by aqueous weight; 3-20% by oil phase weight, which phase contained a hydrophobic liquid oil at 25° C.

International Publication No. WO 2017/059513 A2 (Nanoemulsion compositions and methods) refers to the production of microemulsion droplets of 100-300 nm and of less than 100 nm, which is a process of an oil and water emulsion applicable to the cosmetic products that use surfactants, not to food and other products. Moreover, in this process, Massocare™ HCO 40 (PEG-40 hydrogenated castor oil), Lipocol™ HCO 60 (PEG-60 hydrogenated castor oil), Myrj™ S20, S50, or 5100 (PEG-20, -50, or -100 stearate), and/or PEG-3 oleate were used. Although this group of PEG compounds is allowable for use, it is produced through a process referred to as ethoxy formation, a chemical reaction in which ethylene oxide is added to the substrate. This PEG production is related to ethylene oxide and 1,4-dioxane, a potentially hazardous byproduct. For this reason, PEG is unacceptable in organic cosmetics certified in Europe, and has currently been controversial for its side effects after long-term use, and some types of PEG below 100 have been restricted to use in the products.

Chinese Patent Publication No. CN105476959A (Medium-chain triglyceride (MCT) nano-emulsion and preparation method thereof) refers to MCT being made into a nano-emulsion, thus making it possible to avoid uncomfortable symptoms of nausea, vomiting, diarrhea, or abdominal pain, and the like due to drinking MCT via oral administration. This invention discloses a droplet diameter of less then 100 nm, and the control of the medium chain triglyceride peroxide (MCT) value. This invention employed a high-speed mixer at 100,000 rpm under 5-minute mixing for 3 successive times under 103 Mpa, using a high-pressure homogenizer for 3 successive times. The use of very high speed stirring at 100,000 rpm and homogenization under 103 Mpa, and multiple repetitions with this power makes it impossible to apply on a large scale, as the manufacturing machines cannot meet the required power.

US Patent Publication No. US20170112764A1 (Nanoemulsions having reversible continuous and dispersed phases) refers to the formation of reversible continuous and dispersed phases. Nano-droplets contain an aqueous phase and an oil phase, in which the weight ratio of the aqueous phase to the oil phase is 1:40-100:1. In the microemulsion system of the invention, the aqueous phase is dispersed in the form of nano-droplets in the oil phase, or the oil phase is dispersed in the form of nano-droplets in the aqueous phase. The aqueous phase contains water or an aqueous solution, and water-soluble stabilizers of nano-organic structures. The oil phase contains one type of oil or oil solution, organic thickening agents, and hydrophilic surfactants that have a hydrophilic-lipophilic balance value greater than 8.0. For this invention, the inventors provided the basic indices to form an oil-in-water or water-in-oil phase dispersion system, with no application to any particular agents and no determination of the delivery effects of active agents of the system and the size of the droplets produced.

European Patent No. EP2659903B1 (Nanoemulsion-type ophthalmic composition) related to an ophthalmic composition in the form of a nano-microemulsion, through a process of self-emulsification in an aqueous environment, using one type of oil and specific surfactants, with cyclosporin A as the active agent. This invention disclosed an ophthalmic composition in the form of a microemulsion with a droplet size of less than 200 nm, including cyclosporin; propylene glycol dicaprylocaprat and medium chain triglyceride (C8 to C10) in oil form; polyoxyl 35 hydrogenated castor oil as a surfactant; and sodium dihydrogen photphate or its hydrate, or combination thereof as a buffer. In this invention, the active agent is cyclosporin A, medium chain triglyceride (C8 to C10) is only an additive with a droplet size of less than 200 nm, and the process of the present invention is only applicable to cyclosporin A, and not usable for other compounds, and only applicable on an experimental scale.

In general, the aforementioned processes mainly produce microdroplets of more than than 100 nm, so the dispersion efficiency in water is not high, and the stability time is short, not meeting the requirements if applied to actual product. The studies in experimental models, the use of complex equipments and steps make it difficult to be applicable on an industrial scale and cannot be adjusted to produce a desired droplet size to apply to each product type, especially with the low contents of oils delivered in the system of less than 20% while using PEG, thus do not meet the demand for use.

Therefore, there is a need for a process for production of a microemulsion system that allows the production of oil microdroplets with a droplet size of, as desired by the manufacturer, less than 100 nm, and with an oil content ratio of more than 20%, without using synthetic PEG in the process, which ensures safety and may suggest that the products are of natural origin. The process produces uniform droplets with long-term stability of within two years, having better water dispersibility, and being long-termly stable in the aqueous systems while maintaining a stable structure. The activities of the active agents and the microemulsion droplets produced must be stable during industrial production, and have high applicability to food, pharmaceuticals, and cosmetics.

SUMMARY OF THE INVENTION

It is an objective of the present invention to provide a process for production of a nano-microemulsion system of plant oil triglycerides that allows the production of uniformly sized droplets which are capable of dissolution and long-term stability in water without changes in activities or structures, increasing the efficiency for use of oil triglyceride active agents, namely increasing the absorption and the bioavailability that are applicable on an industrial scale. In particular, a process according to the present invention forms a nano-emulsion system of plant oils without the use of synthetic PEG during the process, ensuring safety and may suggest that the products are of natural origin. The process produces uniform droplets of less than 100 nm, in which the product contains high contents of essential oils of between 20-25% with long-term stability of within two years, better dispersion in water and long-term stability in the aqueous systems while retaining stable structures of of plant oil triglycerides.

To achieve the above objective, the invention provides a process for production of a nano-microemulsion system of plant oil triglycerides, including:

(i) preparing a dispersed phase by heating plant oil triglycerides to a temperature between 60-100° C.;

(ii) preparing a carrier by heating a mixture of propylene glycol monocaprylate and lecithin by a weight ratio of 5-6:1-1.5 to a temperature between 60-100° C. under vacuum by a vacuum rotary evaporator, then cooling to 30° C., followed by, respectively, ultrasonication within 30 minutes, stirring and heating between 60-100° C. within 30 minutes, and introduction of the solution into the vacuum rotary evaporator while stirring at 100° C.;

(iii) adding the carrier to the dispersed phase by a weight ratio of 3-4:1-1.5, wherein the temperature of the dispersed phase after the addition is continuously maintained between 60-100° C. while stirring at 400-800 rpm under vacuum, followed by introduction of the whole mixture through the high-pressure microjet homogenizer;

(iv) adding Tween 80 and Tween 60 to the solution mixture obtained in step (iii) by a weight ratio of 3-4:1-1.5:1-1.5, wherein the temperature of the dispersed phase after the addition is continuously maintained between 60-100° C. while stirring at 400-800 rpm under vacuum;

(v) forming a nano-microemulsion system of plant oil triglycerides by cooling the obtained mixture to 25° C., followed by homogenization of the mixture by ultrasonication using a homogenizer from 30 to 60 minutes to achieve a droplet size of less than 100 nm, quality control of the resultant product by dissolution thereof in water and measurement of the transparency, in which if the required transparency is not met, continue to heat and measure the transparency every 30 minutes until the required transparency is met, then stop the reaction, and emulsification of the solution mixture in an emulsifying device at a stirring rate between 400-800 rpm to obtain a nano-microemulsion system of plant oil triglycerides.

According to an embodiment, in step (ii) of preparing a carrier of the process according to the present invention, the mixture weight ratio of propylene glycol monocaprylate to lecithin is 5:1.

According to an embodiment, in step (iii) of the process according to the present invention, the carrier is added to the dispersed phase by a weight ratio of 3:1.

According to an embodiment, in step (iv) of the process according to the present invention, Tween 80 and Tween 60 are added to the solution mixture obtained in step (iii) by a weight ratio of 3:1:1.

DETAILED DESCRIPTION OF THE PREFERRED EMBODIMENTS

Figure 1:
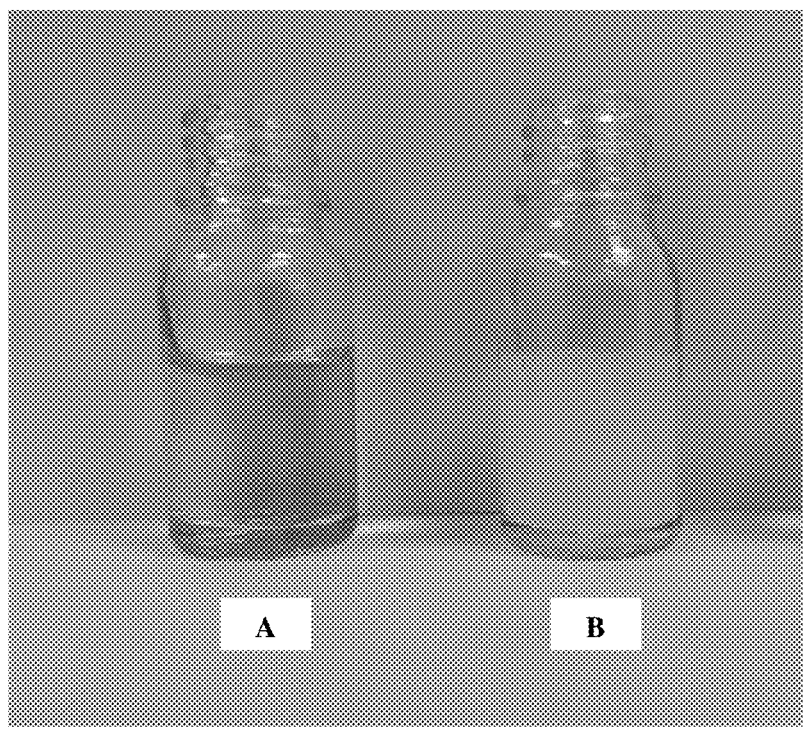
FIG. 1 shows the comparison of the water dispersibility of plant oil triglycerides (A); plant oil triglyceride nano-emulsions (B), obtained by a process according to the present invention

A process for production of a nano-microemulsion system of plant oil triglycerides according to the present invention is performed as follows:
(i) preparing a dispersed phase by heating plant oil triglycerides to a temperature between 60-100° C., the heating allows the dispersed phase to be combined with a better carrier.
(ii) preparing a carrier by heating a mixture of propylene glycol monocaprylate and lecithin by a weight ratio of 5-6:1-1.5, most preferably 5:1, to a temperature between 60-100° C. under vacuum by a vacuum rotary evaporator from 30 to 60 minutes, then cooling to 30° C., followed by, respectively, ultrasonication within 30 minutes, stirring and heating between 60-100° C. within 30 minutes, and introduction of the solution into the vacuum rotary evaporator while stirring at 100° C. from 30 to 60 minutes.

When used, the plant oil triglycerides are likely to be denatured by light, temperature, and often destroyed in the digestive tract. Therefore, there is a demand for a process for production of microdroplets containing oil triglyceride active agents of small size with biofilm, structural stability, nonaggregation, and high solubility. Since the microemulsion system according to the present invention is used in food and pharmaceutical industries, the carriers selected for use must be highly safe, and non-toxic with few side effects. Propylene glycol monocaprylate is a mixture of propylene glycol monoester and fatty acid diester composed mainly of caprylic acids. The contents of the monoester and the diester vary for the two types (Type I and Type II) of propylene glycol monocaprylate with certified safety records. Having properties of a specific soluble carrier for injections, (pharmaceutical and veterinary) solutions, and agents for adjustment and stabilization of viscosity, and for production of microemulsion liquids, propylene glycol monocaprylate helps emulsify and form good microemulsion systems, allowing for an increase in absorption. However, if the carrier is used on the skin in high dosages, it will cause irritation. Therefore, in order to form a microemulsion system that is stable and safe to the users, so that the product can be applied on the skin and administered orally, according to the investigation, the inventors combined propylene glycol monocaprylate with lecithin by a weight ratio of 5-6:1-1.5, most preferably 5:1. Lecithin is a very popular food additive and has been acknowledged as safe to human in Europe. Lecithin is a type of phospholipid by nature, which is found in every cell of the human body. The chemical formula of lecithin shows that lecithin is a fat, of which a structural component, however, is water soluble. This allows lecithin to emulsify plant oil triglycerides, and advocate dispersion thereof in water.

If the ratio of propylene glycol monocaprylate to lecithin is less than 5:1.5, it is possible that the resulting carrier cannot carry the whole oil amount, leading to non-uniform droplet sizes, and the resulting system being unstable and likely to have layer separation. However, if the said ratio is more than 6:1, the lecithin amount will remain in the system, which goes wasted and also makes the system less stable.

In the step of preparing the carrier, the present invention uses propylene glycol monocaprylate and lecithin by a studied ratio that is different from those used in known solutions. In particular, the solution mentioned in US20170112764A1 only relates to a process for determination of the weight ratio of the aqueous phase to the oil phase, which solution is different from that of the present invention, that mentioned in EP2659903B1 to form a microemulsion system for use of cyclosporin A for ophthalmic purpose, which is different from the objective of the present invention to produce microemulsion system of plant oil triglycerides, and that mentioned in CN105476959A of using Ovum *Gallus domesticus Flavus* lecithin for high speed breakdown until the solution is homogenously mixed. Such breakdown makes it difficult to produce uniform molecules, is time-consuming, and affects the quality of lecithin (since lexithin is easy to denature). The use of propylene glycol monocaprylate and lecithin by a ratio studied by the inventors under said conditions helps reduce the impact on the structure of lecithin, while simultaneously propylene glycol monocaprylate also helps increase the capability of carrying active agents, and the loading efficiency compared to the use of lecithin alone.

(iii) adding the carrier to the dispersed phase by a weight ratio of 3-4:1-1.5, most preferably 3:1, wherein the temperature of the dispersed phase after the addition is continuously maintained between 60-100° C. while simultaneously stirring at 400-800 rpm under vacuum from 30 to 60 minutes, followed by introduction of the whole mixture through the high-pressure microjet homogenizer.

By the weight ratio of the carrier to the dispersed phase being 3-4:1-1.5, most preferably 3:1, the reaction yield is most optimal, ensuring that all substances in the dispersed phase are fully carried, and that there is no carrier left in the system.

The incorporation of the carrier now as a mixture of propylene glycol monocaprylate and lecithin in specialized processing steps helps achieve the most optimal contact efficiency and vesiculation of the dispersed phase. The use of the high-pressure microjet homogenizer helps improve the vesiculation efficiency, while simultaneously improving the durability of the biofilms, allowing the lipophilic heads to be fully exposed, and form optimal bonds. The inventors have studied to create a microjet nozzle for integration thereof into the machine in order to not only utilize the high-pressure homogenization to produce droplets, but also allow the droplets to disperse right after formation thereof to avoid droplet aggregation before being added the expanding agents in the next step. This is highly important in improving the stability of the nano system, thereby allowing an increase in yield and stability duration of the system.

(iv) adding Tween 80 and Tween 60 to the solution mixture obtained in step (iii) by a weight ratio of 3-4:1-1.5:1-1.5, most preferably 3:1:1, wherein the temperature of the dispersed phase after the addition is continuously maintained between 60-100° C. while simultaneously stirring at 400-800 rpm under vacuum from 30 to 60 minutes.

By theoretical and empirical studies, the inventors have found that in order to prepare plant oil nano-triglyceride which dissolves well in water, this emulsion needs to have the form of an oil-in-water emulsion. The selection of an emulsifier to improve the stability of the microemulsion system is based on the properties of the microemulsion system (e.g., forms of oil-in-water microemulsion system, water-in-oil microemulsion system, etc.). Therefore, the inventors selected the emulsifier Tween, particularly a combination of Tween 80 (HLB—hydrophilic-lipophilic balance: 15) and Tween 60 (HLB: 14.5), since Tween is a hydrophilic, nontoxic, and highly safe. The addition of Tween 80 and Tween 60 to the solution mixture obtained in step (iii) by a weight ratio of 3-4:1-1.5:1-1.5, most preferably 3:1:1, ensures that the HLB of the emulsion is suitable for it to disperse in the aqueous phase, wherein if the ratio is less than 3:1.5:1.5, the emulsion becomes lipophilic and will make it difficult to disperse well in water, and wherein if the ratio is more than 4:1:1, the emulsion becomes more hydrophilic but less stable.

Since the emulsifier Tween is a molecule with two distinct moieties, a lipophilic moiety and a hydrophilic moiety, it is able to form bonds with oil and the carrier mixture. The lipophilic moiety of Tween forms bonds with plant oil, and the hydrophilic moiety of Tween forms bonds with the hydrophilic moiety of the carrier mixture of propylene glycol monocaprylate and lecithin, which produces microdroplets of plant oil triglyceride nano-emulsions of a structure that protects the activity of plant oil triglycerides well.

According to the most related reference solution disclosed in CN105476959A, only Tween 80 was used, so the dispersion efficiency was not high enough, and the content of dispersed substances was up to only 10%. However, for the process of the present invention, the incorporation of Tween 80 and Tween 60 improves the dispersibility of the compounds, and increases the contents and stability of the compounds.

(v) forming a nano-microemulsion system of plant oil triglycerides by cooling the obtained mixture to 25° C., followed by homogenization of the mixture by ultrasonication using a homogenizer (Ultrasonication) from 30 to 60 minutes to achieve a droplet size of less than 100 nm, quality control of the resultant product by dissolution thereof in water and measurement of the transparency, in which if the required transparency is not met, continue to heat and measure the transparency every 30 minutes until the required transparency is met, then stop the reaction, and lower the temperature slowly until the temperature reached 50° C. or lower, preferably to room temperature, and emulsification of the solution mixture in an emulsifying device at a stirring rate between 400-800 rpm at this temperature to obtain a nano-microemulsion system of plant oil triglycerides.

Nano-droplets tend to agglomerate, thus to disperse these nano-droplets, it is necessary to provide enough energy to break the bondings. The use of the homogenizer as an effective means of dispersing the nano-droplets and reducing the nano-droplet size produces droplets of a smaller and more uniform size. The dispersion and disruption of nano-droplet agglomeration are the result of gas corrosion by ultrasound. As the ultrasound propagates through the solvent, it continuously forms alternating cycles between high and low pressures, which affects the binding forces of the nano-droplets. At the same time, when many bubbles burst, this puts a great pressure on the nano-droplet beams, making it easy for them to get separated easily. From the experiments, the inventors identified the timelines of ultrasonication to help form a droplet structure that meets the product requirements.

By theoretical and empirical studies, the inventors have found that to produce a plant oil triglyceride nano-emulsion with good water solubility, the microemulsion system needs to be in the form of an oil-in-water emulsion. The selection of an emulsifier to improve the stability of the microemulsion system is based on the properties of the microemulsion system (e.g., the forms of oil-in-water microemulsion system, water-in-oil microemulsion system, etc.).

The microemulsion system obtained by a process according to the present invention has a pH of 7-7.4. With this pH value, the microdroplets are stable since in this neutral environment, the bonds between the plant oil triglyceride and the carrier are maintained in the dispersion process, while in the microemulsion system having a pH<7, these bonds weaken leading to the destruction of plant oil triglyceride nano-droplets in the digestive tract.

The nano-microemulsion system of plant oil triglycerides obtained by a process according to the present invention, which has a hydrophilic-lipophilic balance HLB of 13-18, is a hydrophilic microemulsion system. This microemulsion system consists of hydrophilic, and non-aggregated plant oil triglyceride-containing microdroplets, wherein the droplets are uniform in size and stable, which can increase water solubility, thereby improving its applicability to many different types of products.

When comparing the efficiency of the present invention with other most related references, the objectives of the solutions disclosed in US20170112764A1 and EP2659903B1 are different from that of the inventors. Meanwhile, the solution disclosed in CN105476959A employed a high-speed mixer at 100,000 rpm under 5-minute mixing for 3 successive times under 103 Mpa, and a high-pressure followed by homogenization of compounds for 3 successive times. A process that employs very high-speed stirring at 100,000 rpm, homogenization at 103 Mpa, and multiple repetitions with this power is not applicable on a large scale since the manufacturing machines would not meet this power, and at the same time the process would generate a great amount of heat, affecting the quality of the triglyceride. However, in the present invention, the obtained mixture homogenized by ultrasonic waves under cold conditions ensures the quality of triglyceride, and the inventors have studied to combine ultrasonication with emulsification to make it applicable to the process for industrial production in manufacturing instead of using only for experimental models.

EXAMPLES

Example: Producing 200 g of Nano-Microemulsion System of Plant Oil Triglycerides Preparation of a dispersed phase: 10 g of plant oil triglycerides was subjected to stirring at 400 rpm, and heating at 50° C. until uniform.

Preparation of a carrier: a mixture of 25 g of Capryol 90 (Propylene Glycol Monocaprylate) and 5 g of lecithin was subjected to heating to 60° C. in 40 minutes. 30 g of the carrier was added to 10 g of the dispersed phase prepared above. Continue heating the dispersed phase to 60° C. while stirring at 600 rpm under vaccume for 40 minutes.

Tween 80 (sinopol 85 USP) and Tween 60 were added to the mixture in step (iii) by a weight ratio of 3:1:1 in correspondence with 120 g of Tween 80:40 g Tween 60:40 g of the above mixture, wherein the temperature of the dispersed phase after the addition was continuously maintained between 60-100° C., and stirred at 600 rpm under vacuum in 40 minutes to obtain 200 g of mixture.

The obtained mixture was cooled to 25° C. using a homogenizer (Ultrasonic homogenizer) with a power of 200-400 W to homogenize the solution. The ultrasonication duration would affect the droplet size, so in order to achieve droplets of 100-500 nm ultrasonication was performed from 10 to 20 minutes; to achieve droplets of less than 100 nm, ultrasonication was performed from 30 to 60 minutes.

The quality of the resultant product was controlled by dissolution thereof in water and measurement of the transparency, in which if the required transparency had not been met, the product would be heated continuously and the transparency would be measured every 30 minutes until the required transparency was met, then the reaction was stopped, and the temperature was lowered slowly until it reached 50° C. At 50° C., emulsification was performed on the solution mixture at 500 rpm for 30 minutes.

Before filling, 200 g of nano-microemulsion system of plant oil triglycerides with good water dispersibility was collected.

By UV-vis spectrometry, the inventors found that the positions of the peaks of the plant oil triglyceride ingredients and the peaks of the nano-microemulsion system of plant oil triglycerides matched perfectly. This shows that the microemulsion system obtained by the process according to the present invention was able to maintain its structure and the activity of the plant oil triglycerides during nanonization. The UV-Vis spectrometry was used to quantify the plant oil triglyceride content in the microemulsion system. The results show that the concentration of the essential oil in the nano-microemulsion system of plant oil triglycerides fell between 20-25%.

Figure 2:
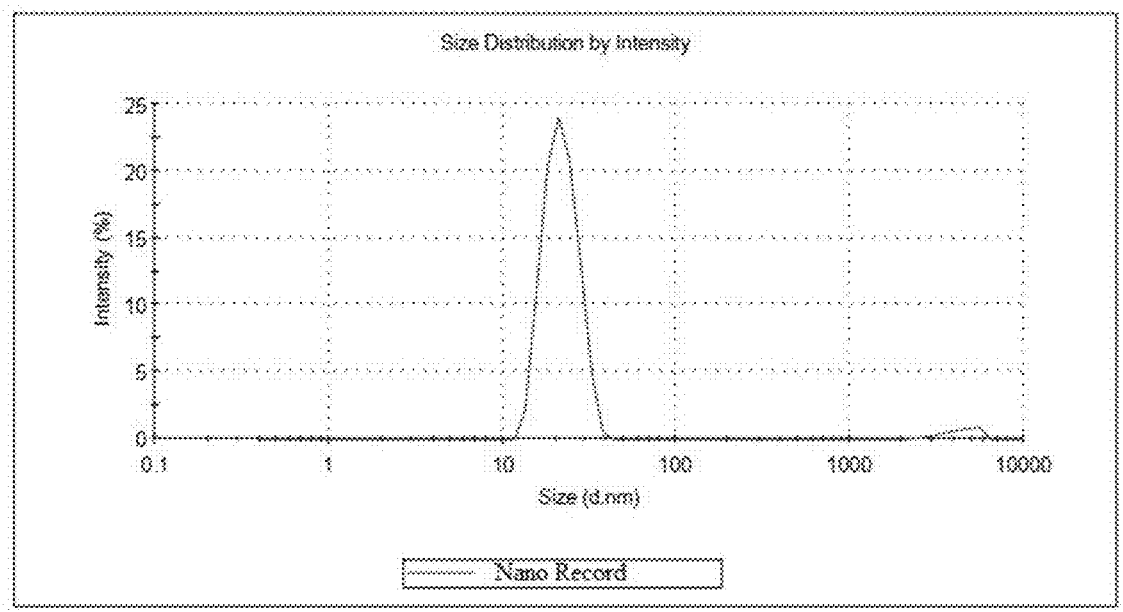
FIG. 2 represents a TEM spectrum by size distribution of the plant oil triglyceride nano-droplets of less than 100 nm, obtained by a process according to the present invention.

The measurement of the size of plant oil triglyceride nano-droplets was conducted by Transmission Electron Microscopy (TEM) as shown in FIG. 2. The figure shows that the droplet size of between 10-50 nm accounts for almost the highest percentage as much as 100% of the solution.

The droplet size was measured by Dynamic Light Scattering (DLS): The suspended droplets in a liquid are constantly subjected to random motions, and the droplet size directly affects the droplet velocity. Smaller droplets move faster than larger ones. In DLS, light passes through the sample, and the scattered light is detected and recorded at a certain angle.

Zeta potential or dynamic potential: The potential between the dispersed phase and the dispersion medium.

The table below shows the data measurements by Dynamic Light Scattering (DLS):

| Plant oil triglyceride nano-emulsion with treatments to achieve a droplet size of less than 100 nm | | Diameter (nm) | % Intensity | Width (nm) |
| --- | --- | --- | --- | --- |
| Average droplet size (d · nm): 22.02 | Peak 1 | 22.02 | 96.7 | 4.791 |
| PdI: 0.136 | Peak 2 | 4418 | 3.3 | 912.0 |
| Blocking rate: 0.939 Evaluation result: good | Peak 3 | 0.00 | 0.00 | 0.00 |

Analysis: Data from this table reflects an average droplet size of 22.02 nm, accounting for 96.7% intensity of the system.

| Size (nm, TEM) | Size (nm, DLS) | Zeta potential (mV) | Stability (month (s)) | Water solubility |
| --- | --- | --- | --- | --- |
| 10-50 | 10-50 | −40 | >24 | good solubility in water; after dissolution in water, the emulsion was stable >60 days |

From the above results, it was shown that the use of the carrier Capryol 90 (Propylene Glycol Monocaprylate) and lecithin in combination with Tween made it possible to obtain the microemulsion system composed of microdroplets of 10-50 nm, good stability (>24 months), good water solubility, and after the dissolution thereof in water, the emulsion was stable for >60 days. A large Zeta potential value indicated that the charged droplets were large and the emulsion tended to be stable.

FIG. 1 shows the comparison of the water dispersibility of between known plant oil triglycerides and a plant oil triglyceride nano-emulsion obtained by a process according to the present invention, in which Vial A shows the known plant oil triglycerides dispersed in water, and Vial B shows the plant oil triglyceride nano-emulsion dispersed in water, obtained by a process according to the present invention. The plant oil triglyceride nano-emulsion obtained by a process according to the present invention completely dispersed in water to produce a transparent, homogeneous solution, while the known plant oil triglycerides were water insoluble and floated on the surface.

FIG. 2 represents a TEM spectrum by size distribution of plant oil triglyceride nano-droplets obtained by a process according to the present invention, which shows the average droplet size of 10-50 nm.

Advantageous Effects of the Invention

The process for production of the nano-microemulsion system of plant oil triglycerides according to the present invention has succeeded in producing a microemulsion system composed of plant oil triglyceride nano-microdroplets of 10-50 nm with uniformity, and good solubility in water while maintaining its structure, and the activity of plant oil triglycerides during nanoization.

The compounds used during the production of plant oil triglyceride nano-emulsion have good dispersibility in water, good safety records, and no toxicity with few side effects. Therefore, the nano-microemulsion system of plant oil triglycerides obtained from the process according to the present invention is safe to use.

The process according to the present invention is simple, easy to implement, and suitable for the practical conditions in Vietnam.

The invention claimed is:
1. A process for production of a nano-microemulsion system of plant oil triglycerides, the method includes:
   (i) preparing a dispersed phase by heating plant oil triglycerides to a temperature between 60-100° C.;
   (ii) preparing a carrier by heating a mixture of propylene glycol monocaprylate and lecithin by a weight ratio of 5-6:1-1.5 to a temperature between 60-100° C. under vacuum by a vacuum rotary evaporator, then cooling to 30° C., followed by, respectively, ultrasonication within 30 minutes, stirring and heating between

60-100° C. within 30 minutes, and introduction of the solution into the vacuum rotary evaporator while stirring at 100° C.;

(iii) adding the carrier to the dispersed phase by a weight ratio of 3-4:1-1.5, wherein the temperature of the dispersed phase after the addition is continuously maintained between 60-100° C. while stirring at 400-800 rpm under vacuum, followed by introduction of the whole mixture through the high-pressure microjet homogenizer;

(iv) adding Tween 80 and Tween 60 to the solution mixture obtained in step (iii) by a weight ratio of 3-4:1-1.5:1-1.5, wherein the temperature of the dispersed phase after the addition is continuously maintained between 60-100° C. while stirring at 400-800 rpm under vacuum; and (v) forming a nano-microemulsion system of plant oil triglycerides by cooling the obtained mixture to 25° C., followed by homogenization of the mixture by ultrasonication using a homogenizer from 30 to 60 minutes to adopt a droplet size of less than 100 nm, quality control of the resultant product by dissolution thereof in water and measurement of the transparency, in which if the required transparency is not met, continue to heat and measure the transparency every 30 minutes until the required transparency is met, then stop the reaction, and emulsification of the solution mixture in an emulsifying device at a stirring rate between 400-800 rpm to obtain a nano-microemulsion system of plant oil triglycerides.

2. The process according to claim 1, wherein in step (ii) of preparing a carrier, the mixture weight ratio of propylene glycol monocaprylate to lecithin is 5:1.

3. The process according to claim 1, wherein in step (iii), the carrier is added to the dispersed phase by a weight ratio of 3:1.

4. The process according to claim 1, wherein in step (iv), Tween 80 and Tween 60 are added to the solution mixture obtained in step (iii) by a weight ratio of 3:1:1.

\* \* \* \* \*